United States Patent [19]

Langham

[11] Patent Number: 4,590,210

[45] Date of Patent: May 20, 1986

[54] COMPOSITIONS FOR TREATMENT OF OCULAR HYPERTENSION

[76] Inventor: Maurice E. Langham, 9 Candlelight Ct., Lutherville, Md. 21093

[21] Appl. No.: 245,735

[22] Filed: Apr. 1, 1981

Related U.S. Application Data

[63] Continuation-in-part of Ser. No. 19,037, Mar. 9, 1979, Pat. No. 4,275,074.

[51] Int. Cl.$^4$ ............................................. A61K 31/225
[52] U.S. Cl. ...................................... 514/548; 514/913
[58] Field of Search ................ 560/144; 424/280, 311, 424/313, 330; 514/548, 913

[56] References Cited

U.S. PATENT DOCUMENTS

| | | | |
|---|---|---|---|
| 3,657,244 | 4/1972 | Mentrup et al. | 424/330 |
| 3,705,233 | 12/1972 | Lunts et al. | 424/45 |
| 3,732,300 | 5/1973 | Lunts et al. | 424/325 |
| 3,808,317 | 4/1974 | Hecht et al. | 424/175 |
| 3,809,714 | 5/1974 | Hussain et al. | 424/311 |
| 3,839,584 | 10/1974 | Hussain et al. | 424/311 |
| 3,868,461 | 2/1975 | Hussain et al. | 424/311 |
| 3,937,838 | 2/1976 | Hetlerlin et al. | 424/311 |
| 3,959,485 | 5/1976 | Windheuser | 514/913 |

OTHER PUBLICATIONS

Langham, "The Pharmacology of the Adrenergic Therapy of Glaucoma," International Glaucoma Symposium, ALBI (France), May 20-24, 1974, pp. 317-331.
Chem. Abst. 89, 99621(a) (1978)—Mandell.
Lewis's Pharmacology—Crossland—4th ed., 1970, pp. 381-382, 386-387.
J. Pharmacol. Exp. Therap. 161: 279-295 (1968)—Patil et al.
J. Pharm. Pharmac., 1969, 21 Suppl. 199S-205S—Farrugia et al.
JADA 92, 748-750 (1976)—Clarlone.
Annals of Ophthal. 3(3), 282-288 (1971)—Lorenzetti.

*Primary Examiner*—Douglas W. Robinson
*Attorney, Agent, or Firm*—Baker & McKenzie

[57] ABSTRACT

Compositions for treating ocular hypertension by topical administration containing α-methyl epinephrine, α-methyl norepinephrine, their $C_1$–$C_8$ alkanoyl diesters and the pharmacologically acceptable acid addition salts thereof are disclosed.

4 Claims, 2 Drawing Figures ature of the present invention is
COMPOSITIONS FOR TREATMENT OF OCULAR HYPERTENSION

CROSS REFERENCES TO RELATED APPLICATION

This is a continuation-in-part of copending U.S. application Ser. No. 019,037, filed Mar. 9, 1979, now U.S. Pat. No. 4,275,074.

TECHNICAL FIELD

The present invention relates to the treatment of ocular hypertension encountered in patients suffering from glaucoma or other ocular disorders. More particularly, this invention relates to compounds and compositions for effectively lowering mammalian intraocular pressure.

BACKGROUND ART

Increased intraocular tension is caused by a disruption of the normal mechanisms regulating the pressure within the eye of a mammal. A great deal of progress has recently been made in understanding these mechanisms. It is now well established that aqueous humor drains from the eye through a sieve-like barrier into a complex network of small vessels. Ocular hypertension is directly related to rate of secretion of aqueous humor into the eye and to outflow resistance of the drainage channels, although the mechanisms of these phenomena remain to be elucidated.

One of the diseases of the mammalian eye characterized by increased intraocular tension is glaucoma. Manifestations of glaucoma include hardening of the globe, excavation of the optic disc and restriction of the field of vision. Glaucoma causes blindness and, in Western man, indeed, is one of the leading causes of blindness.

The presently available methods of therapy for the treatment of glaucoma consist mainly of the administration of miotics, the adrenergic drug epinephrine, carbonic anhydrase inhibitors, and/or surgery. Surgery usually is reserved for the treatment of the less common, acute congestive form of glaucoma and for those cases of chronic open-angle glaucoma that do not respond to drug therapy. The carbonic anydrase inhibitors seldom suffice as the sole means of therapy and are used in conjunction with miotics in the therapy of chronic glaucoma and as a preparatory measure to reduce intraocular pressure prior to surgery.

At the present, the mainstay of glaucoma therapy is the topical administration of miotics. The most commonly employed miotic is pilocarpine. This drug has certain disadvantages, namely, the need for frequent administration, usually around the clock instillation. In addition, pilocarpine causes a "pin point" pupil with associated restriction of vision. Incidentally, the loss of motility of the iris, as manifested by the "pin point" pupil, when miotics are employed is pronounced disadvantage of all drugs presently used in the treatment of glaucoma. In addition, tachyphylaxis or tolerance to the drug is not uncommon, and increasingly stronger solutions must be used for continued therapy. Often, tolerance develops even to the uppermost dose level available.

In recent years the adrenergic drug epinephrine has been used as a valuable alternate or substitute to the miotics. It has been of especial value in the younger glaucoma patient, where the spasm of the ciliary muscle induced by miotic treatment is particularly disabling. Epinephrine is usually applied twice a day either with or without other drugs. Unfortunately, the drug has to be used in relatively high concentrations, has a mydriatic effect, and toleration of the ocular tissues to epinephrine usually is approximately two years. Epinephrine also induces undesirable side effects of congestive hyperemia of the conjunctival vessels due, principally, to its $\beta$-adrenoceptor agonist activity. U.S. Pat. No. 3,809,714 to Hussain et al. discloses the activity of dipivalyl epinephrine for the treatment of glaucoma; however, this particular compound also elicits a mydriatic (pupil dilation) response by stimulation of $\alpha$-adrenergic receptors.

Mydriasis is particularly undesirable in the treatment of narrow-angle glaucoma since known mydriatic compounds such as epinephrine, norepinephrine and dipivalyl epinephrine provoke occlusion of the irido-corneal angle with a resulting increased resistance to aqueous flow and a consequent rise in ocular tension in spite of a reduced aqueous flow.

Therefore, there is an outstanding need for new therapeutic agents and, indeed, new approaches which can be employed in the treatment of ocular hypertension, particularly in cases of glaucoma, without the attendant disadvantages of the presently available measures. The present invention provides a new pharmacological approach to the treatment of ocular hypertension utilizing $\alpha$-methyl derivatives of epinephrine and norepinephrine that have been found to exhibit an unexpectedly high activity in reducing mammalian intraocular pressure without eliciting attendant undesirable pupillary and accommodative responses at concentrations effective in reducing intraocular pressures, and that are not substrates for monoamine oxidase and consequently are not readily destroyed after administration.

The unexpected nature of the present invention is further underscored by literature reports that such $\alpha$-methyl derivatives are relatively inactive in other tissues as compared to epinephrine and norepinephrine, such as for example, J. Pharmacol. Exp. Therap. 160:279–295 (1968); J. Pharm. Pharmac., 1969, 21, Suppl., 1-9S-205S; and JADA, 92:748–750 (1976). In Annals of Ophthalmology, 3, No. 3, 282 (March 1971), it is reported that the $\alpha$-methyl derivatives of epinephrine and norepinephrine (dioxyephedrine and nordefrin, respectively) are inactive in lowering intraocular pressure.

SUMMARY OF THE INVENTION

The present invention contemplates ophthalmic compositions effective for lowering mammalian intraocular tension and containing as an active ingredient $\alpha$-methyl epinephrine, $\alpha$-methyl norepinephrine, an aliphatic ester thereof or their addition salts with physiologically tolerable (pharmacologically acceptable) acids, as well as two specific active ingredients themselves.

In particular, the present compositions in unit dosage form contain as an active ingredient about 0.01 to about 5 milligrams, preferably about 0.02 to about 2 milligrams, of a catecholamine which is a member of the group consisting of the compounds represented by the general formula

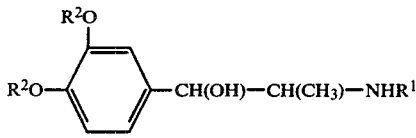

wherein $R^1$ can be hydrogen or methyl and wherein $R^2$ can be hydrogen or an acyl moiety containing 1 to 8 carbon atoms, inclusive. The foregoing compounds can be used in a free base form or as pharmacologically acceptable acid addition salts. The present compositions also contain a diluent amount of an ophthalmic vehicle.

The instant invention also contemplates the specific compounds of the above formula wherein $R^1$ is methyl or hydrogen and $R^2$ is pivaloyl.

The foregoing active ingredients are effective in lowering mammalian intraocular pressure, when administered in an appropriate dosage form, either singly or in combination with other known anti-glaucomatous drugs. Relatively low concentrations of the aforementioned α-methyl derivatives produce a long-lasting decrease of intraocular pressure in the mammalian eye with substantially no dilation of the pupil. Moreover, these α-methyl derivatives of epinephrine and norepinephrine are effective in decreasing the intraocular pressure at much lower concentrations than epinephrine and norepinephrine.

BRIEF DESCRIPTION OF THE DRAWINGS

In the drawings forming a portion of the specification.

DETAILED DESCRIPTION OF THE INVENTION

Figure 1:
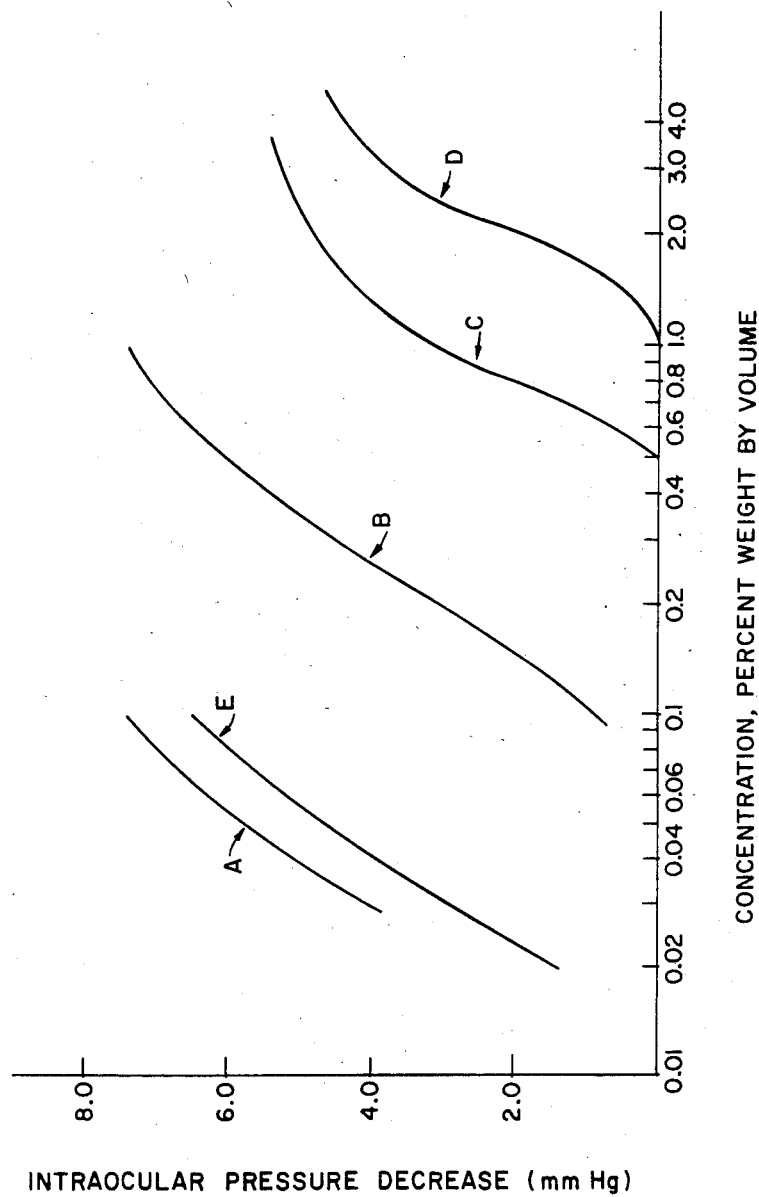
FIG. 1 shows the dose response curves for dipivaloyl α-methyl norepinephrine, α-methyl norepinephrine, epinephrine, norepinephrine and dipivaloyl α-methyl epinephrine.

The compositions of this invention can contain as the active ingredient α-methyl norepinephrine, α-methyl epinephrine, or acylated derivatives (esters) of these compounds or the pharmacologically acceptable acid addition salts thereof in a conventional ophthalmic vehicle which serves as a diluent for effective unit dosage forms. Some of the active ingredients are believed to be new, while others are known compounds, some of which are commercially available under the designations Cobefrin, Nordefrin, Corbasil, and Carbocaine. Preparation of compounds contemplated as active ingredients for the purposes of the present invention is also disclosed in U.S. Pat. No. 3,904,671 to Minatoya et al. Preparation of those active ingredients believed to be new are illustrated by typical syntheses given in Examples 1 and 2.

The acylated derivatives of α-methyl epinephrine and α-methyl norepinephrine may be hydrolyzed to α-methyl epinephrine and α-methyl norepinephrine or to either or both of the corresponding monoesters while in the mammalian eye; however, the presence of the ester group or groups on the acylated derivatives enhances the chemical stability and the lipid solubility of these compounds, and thus facilitates the transport thereof into the eye.

Illustrative of the acyl moieties that can be present are formyl, acetyl, propionyl, butyryl, isobutyryl, valeryl, isovaleryl, pivaloyl, caproyl, capryloyl, and the like.

To prepare the acylated derivatives of the compounds shown in the previous formula, the 3-OH and 4-OH groups of the compounds themselves, or of their precursors, can be esterified using conventional acylation conditions by acylating agents such as anhydrides, mixed anhydrides, or the chloride of the appropriate alkanoic acid.

The compounds herein contemplated as active ingredients have two asymmetric carbon atoms and thus each compound can exist in four epimeric forms, i.e., as the (−)erythro, (+)erythro, (−)threo, or (+)threo stereoisomer. For the purposes of the present invention, the particular stereoisomers can be used individually or as mixtures.

The foregoing compounds can exist and can be used in the non-protonated or free base form as well as in the protonated or acid addition salt form, depending on the pH of the environment therefor.

Physiologically tolerable acid addition salts of the foregoing compounds can be prepared by the neutralization of the free base form with an appropriate amount of an organic or inorganic acid, examples of which are hydrochloric, hydrobromic, phosphoric, acetic, lactic, salicylic, glycolic, ascorbic, succinic, tartaric, maleic, malic, pamoic, citric, and the like. The preferred acid addition salts for the present purposes are selected from hydrochloride, ascorbate, and maleate, and are prepared from hydrochloric acid, ascorbic acid and maleic acid, respectively.

The neutralization can be carried out by a variety of procedures known to the art to be generally useful for the preparation of amine acid addition salts. The choice of the most suitable procedure will depend on a variety of factors including convenience of operation, economic considerations, and particularly the solubility characteristics of the particular free base, the acid, and the acid addition salt.

For example, if the acid is soluble in water, the free base can be dissolved in water containing an equivalent amount of the acid, and thereafter, the water can be removed by evaporation; in some instances, the salt precipitates from the aqueous solution, particularly when cooled, and evaporation is not necessary. If the acid is soluble in a relatively non-polar solvent, for example, diethyl ether or diisopropyl ether, separate solutions of the acid and free base in such a solvent can be mixed in equivalent amounts, whereupon the acid addition salt will usually precipitate because of its relatively low solubility in the non-polar solvent. Alternatively, the free base can be mixed with an equivalent amount of the acid in the presence of a solvent of moderate polarity, for example, a lower alkanol, a lower alkanone, or a lower-alkyl ester of a lower alkanoic acid. Examples of these solvents are ethanol, acetone, and ethyl acetate, respectively. Subsequent admixture of the resulting solution of acid addition salt with a solvent of relatively low polarity, for example, diethyl ether or hexane, will usually cause precipitation of the acid addition salt. The formation of acid addition salts can also be utilized for upgrading the free bases prior to formulation, if necessary.

The compositions of the present invention can be administered topically to the eye in unit dosage form, as ophthalmic solutions (including physiological saline), or as ophthalmic ointments, creams, gels, or dispersions. Typical ointment bases suitable for this purpose include white petrolatum and mineral oil or liquid petrolatum. Slow release polymers or depo systems incorporating the described -methyl derivatives of epinephrine and/or norepinephrine can also be employed if desired.

The term "unit dosage form" as used herein refers to physically discrete units suitable as unitary dosages for humans and animals, each unit containing a predetermined quantity of active material calculated to produce the desired therapeutic effect in association with the required diluent, i.e., carrier, or vehicle. The specifications for the novel unit dosage forms of this invention are dictated by and are directly dependent on (a) the unique characteristics of the active material and the particular therapeutic effect to be achieved, and (b) the limitations inherent in the art of compounding such active material for therapeutic use in humans and animals, as disclosed in detail in the specification, these being features of the present invention. The unit dosage forms can be manually delivered to the eye as drops, or by suitable microdrop or spray devices typically providing a metered dose of medication.

The amount of active ingredient that is to be administered depends on the age, weight of the patient, the particular condition to be treated, the frequency of administration, and the like. The human dose can range from about 0.01 to about 5 milligrams daily given as a single dose or in 3 or 4 divided doses. Preferably, the daily adult human dose is from about 0.02 to about 2 milligrams. Veterinary dosages will correspond to human dosages.

Suitably, the concentration of the active ingredient in the solution is within the range of 0.001 to 0.5 weight percent by volume; this range is preferably from about 0.001 to about 0.15 weight percent by volume. Higher concentrations of solutions, as for example, those at about 0.2 to about 0.5 weight percent by volume, as well as lower concentrations can be employed (as for example, in a solution in combination with a miotic, e.g., pilocarpine, or with a sympathomimetic amine), provided that the ultimate solution concentrations of the present α-methyl derivatives of epinephrine or norepinephrine together with the exogenous sympathomimetic amines and the miotic are effective in lowering intraocular pressure and are non-irritating.

In the treatment of glaucoma in man, the antiglaucoma compositions of this invention can be initially administered in unit dosage form, i.e., dropwise, three times daily. After the patient has responded, as determined by a sustained lowering of intraocular pressure and significant alleviation of the manifestations of glaucoma, the daily regimen can be reduced to once a day or once every other day or less, as a maintenance dose for continued effect.

As stated hereinbefore, the concentration of active ingredient in the present compositions can be varied. It is necessary, however, that the active ingredient be present in an amount such that a suitable dosage will be delivered to the patient. While several unit dosage forms can be administered at about the same time, administration at appropriate periodic intervals to achieve the desired effect is preferable. Activity increases with concentration of the active ingredient in the unit dose, and in general, it has been found to be desirable to maintain unit dosage concentrations below that level at which any systemic action due to the α-methyl derivative present is observable. Such concentrations generally fall within the above-described ranges; however, it is to be understood that these general ranges can be modified in certain instances to suit the needs and responses of an individual patient. Therefore, any dose which will produce the desired effect without irritation, and furthermore, falls below the toxic dose, in most instances below the $LD_{50}$ dose of the particular α-methyl derivative present, can be employed.

For the present purposes sterile physiological saline is a suitable vehicle. Other suitable ophthalmic vehicles are well known in the art and are fully described in such standard reference works as *Remington's Pharmaceutical Sciences*, Martin and Cook, Mack Publishing Co., Easton, Pa., 13th edition (1965). The following is a suitable example. (The percentages in the following examples refer to a percent weight by volume.)

| STERILE VEHICLE | |
|---|---|
| Ingredient | Percent w/v |
| Oxine sulfate | 0.01 |
| Sodium bisulfite | 0.3 |
| Phenylmercuric acetate | 0.002 |
| Sodium hydroxide or hydrochloric acid to ph. 3.5–6 | |
| Water, q.s. | |

In the foregoing composition, the oxine sulfate (8-hydroxy-quinolone sulfate) and the sodium bisulfite act as antioxidants and the concentration thereof can vary tenfold (the former up to about 0.1 percent, and the latter down to about 0.03 percent). In addition to these specific antioxidants, any ophthalmic antioxidant can be employed. These are more fully described in Remington (supra).

Phenyl mercuric acetate is employed as a preservative. Any preservative suitable for ophthalmic formulation such as those described in Remington (supra) can be employed. A pH value range from about 3.5–8 can be employed, although a pH value within the physiological range is preferred. When employing a buffered system, it is preferred to utilize a pH value of about 6.0 to about 8. With a buffered system, pH value is conventionally adjusted by adjusting the concentration and, thereupon, altering the ratio of the buffered tonicity so as to maintain an isotonic solution. Although buffers can be used at varying pH values, when the pH value is less than 6.0, sodium hydroxide or hydrochloric acid can conveniently be employed for adjustment. When using a buffered system it is preferred to adjust the range to that of the physiological pH value range of about 6 to 7.5 or 8. U.S. Pat. No. 3,149,035 to Riegelman sets forth additional specific suitable sterile vehicles that can be employed in formulating the compositions of this invention.

The pH value of the foregoing, specific sterile vehicle can be adjusted using base or acid. Also, standard buffering agents such as those described in Remington (supra) or in the Merck Index, 9th ed., page Misc. 97, (1976), can be used so long as these buffering agents are suitable for an opthalmic formulation, can be utilized.

Typical formulations effective for lowering mammalian intraocular tension are set forth hereinbelow:

| Ingredient | Percent w/v |
|---|---|
| FORMULATION I | |
| (−)erythrp-α-methyl epinephrine | 0.05 |
| Oxine sulfate | 0.01 |
| Sodium bisulfite | 0.3 |
| Boric acid | 0.8 |
| Sodium borate | 0.6 |
| Phenylmercuric acetate | 0.002 |
| Water, q.s. | |
| FORMULATION II | |
| (−)erythro-α-methyl norepinephrine | 0.20 |
| Oxine sulfate | 0.01 |
| Sodium bisulfite | 0.3 |
| Boric acid | 0.8 |
| Sodium borate | 0.6 |
| Phenylmercuric acetate | 0.002 |
| Water, q.s. | |

As mentioned hereinbefore, the compositions of this invention can also be formulated and administered as ophthalmic ointments compounded, for example, by mixing finely milled powdered ingredients with a small amount of white petrolatum and livigating or otherwise combining until a uniform distribution is achieved. The balance of white petrolatum is added by geometric addition until the desired dosage form is made.

Melting points were determined and elemental analyses performed on the hydrochloride derivatives of the two new catecholamines used in the compositions of this invention. These data are set out hereinbelow:

3,4-Dipivaloyl α-Methyl Norepinephrine Hydrochloride

A melting point of 200°–202° C. was found. An elemental analysis gave the following results expressed as weight percent:

| | C | H | N |
|---|---|---|---|
| Calc'd. ($C_{19}H_{30}NO_5Cl$) | 58.83 | 7.74 | 3.61 |
| Found | 58.74 | 7.85 | 3.61 |

3,4-Dipivaloyl α-Methyl Epinephrine Hydrochloride

A melting point of 194°–196° C. was found. An elemental analysis gave the following results expressed as weight percent:

| | C | H | N |
|---|---|---|---|
| Calc'd. ($C_{20}H_{32}NO_5Cl$) | 59.78 | 7.97 | 3.49 |
| Found | 59.73 | 8.01 | 3.51 |

The compositions of the present invention have been tested in standard laboratory animals and found to possess the capability of lowering mammalian intraocular pressure without substantial mydriasis. The effect of different concentrations of racemic α-methyl norepinephrine hydrochloride in 0.9 percent (w/v) physiological saline applied singly to one eye of conscious rabbits is summarized in Table I, below.

TABLE I

The Ocular Response to a Single Topical Application of α-Methyl Norepinephrine to One Eye (Exp) of Conscious Rabbits

| Conc'n, Percent Wt. by Volume | Intraocular Pressure (mm Hg) | | | | Pupil Diameter (mm) | | | |
|---|---|---|---|---|---|---|---|---|
| | Control Eye | Exp. Eye | Mean Δ | | Control Eye | Exp. Eye | Mean Δ | |
| 0   | 21.2 ± 0.6 | 21.0 ± 0.6 | 0.2 ± 0.01 | (10) | 3.4 ± 0.13 | 3.5 ± 0.18 | 0.05 ± 0.1 | (10) |
| 0.1 | 21.4 ± 1.6 | 20.5 ± 1.3 | 0.9 ± 0.3  | (4)  | 3.7 ± 0.25 | 4.6 ± 0.47 | 0.9 ± 0.4  | (4)  |
| 0.3 | 21.0 ± 0.6 | 16.5 ± 0.3 | 4.5 ± 0.3  | (4)  | 3.1 ± 0.3  | 4.4 ± 0.9  | 1.2 ± 0.63 | (4)  |
| 0.5 | 21.5 ± 0.7 | 15.5 ± 0.8 | 6.0 ± 0.3  | (4)  | 3.0 ± 0.1  | 3.9 ± 0.4  | 0.9 ± 0.5  | (4)  |
| 0.8 | 22.5 ± 1.4 | 15.7 ± 1.1 | 6.8 ± 0.7  | (6)  | 3.7 ± 0.27 | 4.8 ± 0.42 | 1.1 ± 0.30 | (6)  |
| 1.0 | 21.6 ± 0.7 | 14.3 ± 0.6 | 7.4 ± 0.7  | (10) | 3.7 ± 0.21 | 7.2 ± 0.51 | 3.4 ± 0.4  | (10) |

The reported pressure and pupillary responses are the means of the maximal responses based on the time courses of the responses in pairs of eyes of individual rabbits. The number in parentheses ) denotes the number of experimental subjects.

The mean time course of the ocular response to a 0.5 percent (w/v) solution of racemic α-methyl norepinephrine in 0.9 percent (w/v) physiological saline applied unilaterally to conscious rabbits is shown in Table II, below.

TABLE II

The Effect of a Single Application of 0.5 Percent (w/v) α-Methyl Norepinephrine on the Intraocular Pressure of Six Conscious Rabbits

| Time, hours | Intraocular Pressure (mm Hg) | | |
|---|---|---|---|
| | Control Eye | Treated Eye | Mean Δ Control - Exp. |
| 0 | 23.2 ± 1.3 (6) | 22.8 ± 1.4 (6) | 0.3 ± 0.3 (6) |
| 1 | 23.0 ± 1.6 (6) | 20.2 ± 1.6 (6) | 2.8 ± 0.9 (6) |
| 3 | 23.0 ± 1.3 (6) | 15.8 ± 1.3 (6) | 7.2 ± 0.9 (6) |
| 4 | 23.0 ± 1.4 (6) | 16.7 ± 1.2 (6) | 6.3 ± 1.2 (6) |

The drug was applied unilaterally (treated eye). In the third column is reported the mean pressure difference in pairs of eyes of individual rabbits. The number in parentheses ( ) denotes the number of experimental subjects.

Tables III A, III B, IV and V, below, summarize the experimental results using racemic α-methyl epinephrine, diester of α-methyl epinephrine, and diester of α-methyl norepinephrine in 0.9 percent (w/v) physiological saline. These results strikingly demonstrate the unexpected lack of pupillary dilation while reducing intraocular pressure. The observed lack of pupillary response is in marked contrast to the ocular response to dipivaloyl ester of epinephrine as reported by Hussain et al. in U.S. Pat. No. 3,809,714.

TABLE III A

The Intraocular Pressure Response of Eight Conscious Rabbits to a Single Application of 0.5 Percent (w/v) Solution of α-methyl Epinephrine Hydrochloride

| Time, hours | Intraocular Pressure (mm Hg) | | |
|---|---|---|---|
| | Control Eye | Exp. Eye | Mean Δ Control - Exp. |
| 0    | 22.6 ± 0.8 | 22.7 ± 0.6 | −0.1 ± 0.2 |
| 0.5  | 22.8 ± 0.9 | 19.4 ± 1.3 | 3.3 ± 0.8 |
| 1.0  | 21.8 ± 1.0 | 15.9 ± 1.2 | 5.9 ± 0.6 |
| 3.0  | 20.1 ± 0.9 | 14.1 ± 0.5 | 6.0 ± 0.8 |
| 5.0  | 20.1 ± 0.7 | 14.6 ± 0.6 | 5.5 ± 0.7 |
| 24.0 | 23.5 ± 0.9 | 22.9 ± 0.9 | 0.6 ± 0.1 |

The drug was applied unilaterally (Exp. Eye) at T = 0 hr. In the third column is reported the mean pressure difference between pairs of eyes of individual rabbits.

TABLE III B

The Lack of Mydriatic Response in Eight
Conscious Rabbits to a Single Application
of 0.5 Percent (w/v) Solution of
α-Methyl Epinephrine Hydrochloride

| Time, hours | Pupil Diameter (mm) | | |
|---|---|---|---|
| | Control Eye | Exp. Eye | Mean Δ Exp. - Control |
| 0 | 3.2 ± 0.1 | 3.1 ± 0.1 | −0.1 ± 0.1 |
| 0.25 | 3.2 ± 0.1 | 3.2 ± 0.1 | 0.0 ± 0.1 |
| 0.5 | 3.2 ± 0.2 | 3.2 ± 0.1 | 0.0 ± 0.1 |
| 1 | 3.2 ± 0.2 | 3.4 ± 0.1 | 0.2 ± 0.1 |
| 3 | 3.2 ± 0.2 | 3.1 ± 0.1 | −0.1 ± 0.1 |
| 5 | 3.2 ± 0.1 | 3.1 ± 0.1 | −0.1 ± 0.1 |

The active ingredient was applied unilaterally (Exp. eye) at T = 0 hr. In the third column is reported the mean pupil diameter differences in pairs of eyes. This data was taken on the same animals and during the same study as shown in Table III A, above.

TABLE IV

The Intraocular Pressure Response of Six
Conscious Rabbits to a Single Application
of 0.1 Percent (w/v) Solution of
Dipivalyl Ester of α-Methyl Epinephrine

| Time, hours | Intraocular Pressure (mm Hg) | | |
|---|---|---|---|
| | Control Eye | Exp. Eye | Mean Δ Control - Exp. |
| 0 | 21.6 ± 0.5 | 21.7 ± 0.5 | −0.1 ± 0.1 |
| 1.0 | 21.8 ± 0.5 | 15.9 ± 1.0 | 5.9 ± 1.4 |
| 3.0 | 20.3 ± 0.5 | 12.8 ± 0.6 | 7.5 ± 0.7 |
| 5.0 | 19.9 ± 0.6 | 13.2 ± 0.6 | 6.7 ± 0.8 |
| 24.0 | 20.0 ± 0.6 | 18.4 ± 0.4 | 1.5 ± 0.3 |

The active ingredient was applied unilaterally (Exp. Eye) at T = 0 hr. In the third column is reported the mean pressure difference between pairs of eyes of individual rabbits.

TABLE V

The Intraocular Pressure Response of Four
Conscious Rabbits to a Single Application
of 0.1 Percent (w/v) Solution of
Dipivalyl Ester of α-Methyl Norepinephrine

| Time, hours | Intraocular Pressure (mm Hg) | | |
|---|---|---|---|
| | Control Eye | Exp. Eye | Mean Δ Control - Exp. |
| 0 | 20.8 ± 0.7 | 20.5 ± 0.7 | 0.3 ± 0.1 |
| 1.0 | 21.3 ± 0.6 | 17.1 ± 0.4 | 4.2 ± 0.4 |
| 3.0 | 20.7 ± 0.8 | 11.8 ± 0.3 | 8.9 ± 1.1 |
| 5.0 | 20.4 ± 0.6 | 12.1 ± 0.3 | 8.4 ± 0.8 |
| 24.0 | 20.8 ± 0.4 | 18.3 ± 0.4 | 2.5 ± 0.2 |

The active ingredient was applied unilaterally (Exp. Eye). In the third column is reported the mean pressure difference between pairs of eyes of individual rabbits.

The unexpected nature of the present invention is further illustrated in FIG. 1 by the dose response curves for α-methyl derivatives of norepinephrine and epinephrine as compared to the dose response curves for epinephrine and norepinephrine. Data for the foregoing curves were obtained by applying a solution of the compound in 0.9 percent (w/v) physiological saline to eyes of individual rabbits.

Figure 2:
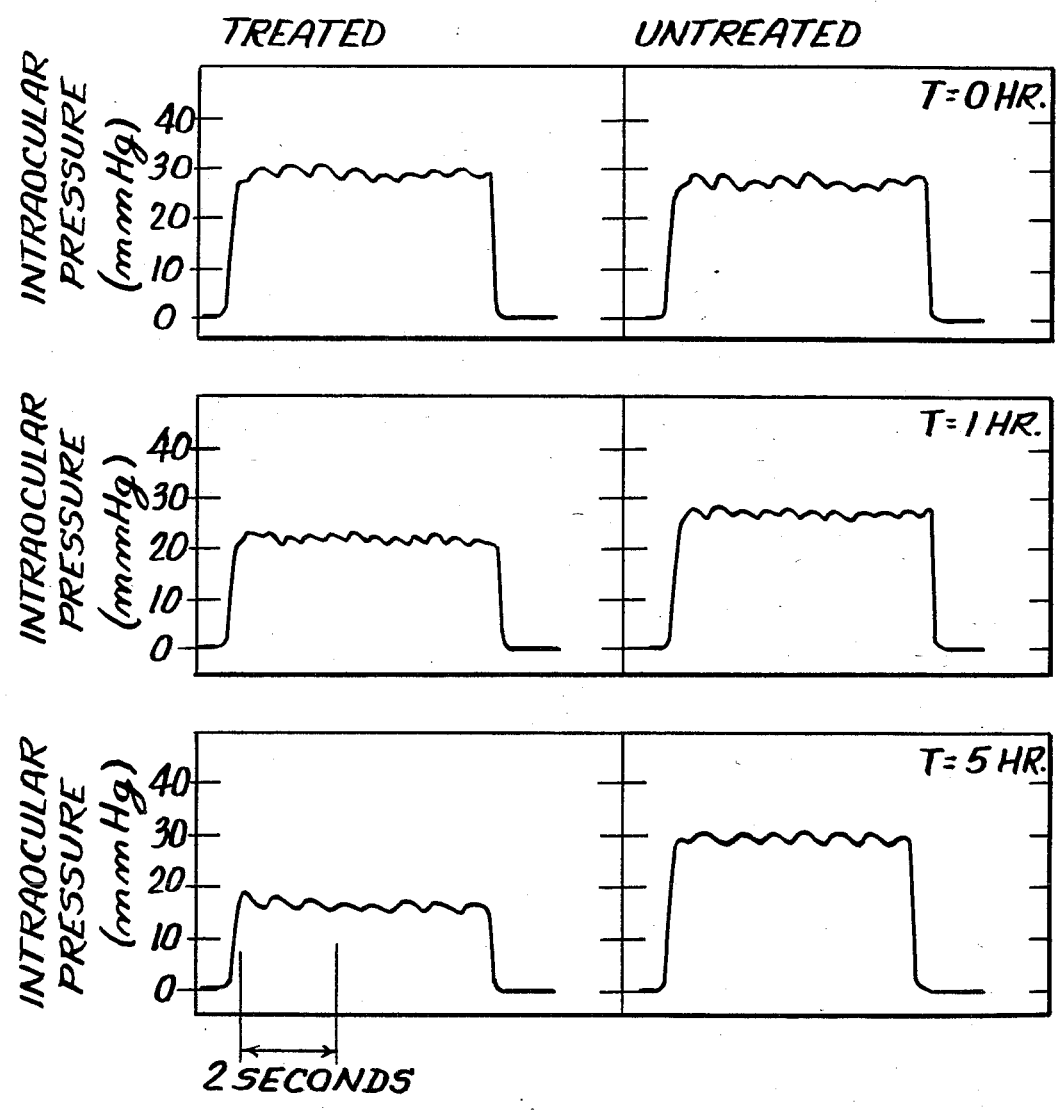
FIG. 2 shows tonometric recordings of the intraocular pressure of both eyes of an individual subject following the application of 1 drop of 0.1 weight percent by volume of dipivaloyl α-methyl epinephrine to one eye (treated) at a treatment time of zero hours (T=0 hr.) with the other eye (untreated) serving as a control.

Tonometry and tonography studies were performed on normal healthy volunteers using an instrument denominated The Alcon pneumatonograph, available from Alcon Laboratories, Fort Worth, Tex. One drop of proparacaine (0.5 percent w/v) was applied to each eye prior to taking tonometric readings. The tonometer was calibrated by a manometric standard prior to initiation of these studies and checked on an air standardizer on each day of use. A typical set of tonometric recordings for treated and untreated eyes is illustrated in FIG. 2. Pupil diameters were measured under normal laboratory light.

Each drug discussed hereinafter was dissolved in sterile physiological saline.

Table VI summarizes the time course of the intraocular pressure and the pupil response to one drop of 0.1 percent (w/v) dipivaloyl α-methyl epinephrine hydrochloride in seven subjects from the time of application (T=0 hours) through a time 24 hours thereafter (T=24 hours). The seventh subject was an ocular hypertensive with no evidence of glaucomatous field loss or pathological cupping of the disc. The intraocular pressures of the treated eyes were significantly decreased at 1 and 5 hours and had recovered by 24 hours.

A solution of timolol maleate given under similar conditions to normal subjects gave no demonstrable pressure response at a concentration of 0.1 percent (w/v) timolol but did give a pressure response at a 0.5 percent (w/v) concentration (Table VII).

The almost complete lack of pupillary response in the normal subject given 0.1 percent (w/v) dipivaloyl α-methyl epinephrine hydrochloride is also summarized in Table VI. This lack of pupillary response is similar to that shown by timolol. However, it differs from the mydriatic response induced by dipivaloyl epinephrine under similar conditions. In this respect, it was found that 0.1 percent (w/v) dipivaloyl epinephrine had no effect on intraocular pressure in normal subjects and that 0.5 percent (w/v) dipivaloyl epinephrine induced a significant decrease of intraocular pressure which was associated with marked mydriasis. The time course of the intraocular pressure response to dipivaloyl epinephrine differed from that to dipivaloyl α-methyl epinephrine hydrochloride in that the former drug gave no significant pressure response at 1 hour.

Data based on tonographic studies made on these subjects indicate that the ocular hypotensive response to the dipivaloyl α-methyl epinephrine hydrochloride is associated with an increase in the outflow facility and a reduction in the rate of formation of the aqueous humor. In studies with timolol, no effect on the outflow facility was found (Table VII).

TABLE VI

The Ocular Response to a Single Topical Application of
One Drop of 0.1 Percent Dipivaloyl α-Methyl Epinephrine
to One Eye (Treated) of Seven Human Subjects*

| | | 0 Hours | | 1 Hour | | 5 Hours | | 24 Hours | |
|---|---|---|---|---|---|---|---|---|---|
| | | Control Eye | Treated Eye | Control Eye | Treated Eye | Control Eye | Treated Eye | Control Eye | Treated Eye |
| Intraocular | | 16 | 16 | 16 | 12 | 16 | 12 | 16 | 19 |
| Pressure | | 18 | 18 | 18 | 14 | 18 | 13 | 17 | 14 |
| (mm Hg) | | 17 | 17 | 16 | 14 | 17 | 15 | 18 | 17 |
| | | 15 | 15 | 15 | 12 | 15 | 13 | 15 | 15 |
| | | 20 | 21 | 20 | 18 | 20 | 17 | 20 | 20 |
| | | 15 | 15 | 16 | 13 | 16 | 13 | 16 | 14 |
| | | 27 | 27 | 27 | 21 | 27 | 16 | 26 | 26 |
| Pupil | | 3 | 3 | 3 | 3.5 | 3 | 3 | 3 | 3 |

TABLE VI-continued

The Ocular Response to a Single Topical Application of
One Drop of 0.1 Percent Dipivaloyl α-Methyl Epinephrine
to One Eye (Treated) of Seven Human Subjects*

|  | 0 Hours | | 1 Hour | | 5 Hours | | 24 Hours | |
|---|---|---|---|---|---|---|---|---|
|  | Control Eye | Treated Eye | Control Eye | Treated Eye | Control Eye | Treated Eye | Control Eye | Treated Eye |
| Diameter (mm) | 4 | 4 | 4 | 4 | 4 | 4 | 4 | 4 |
|  | 3.5 | 3.5 | 3.5 | 3.5 | 3.5 | 3.5 | 3.5 | 3.5 |
|  | 3 | 3 | 3 | 4 | 3 | 3.5 | 3 | 3 |
|  | 4 | 4 | 4 | 4 | 4 | 4 | 4 | 4 |
|  | 3.5 | 3.5 | 3.5 | 4.5 | 3.5 | 4.5 | 3.5 | 3.5 |
|  | 3 | 3 | 3 | 3 | 3 | 3.5 | 3 | 3 |

*The subject whose 0 hour pupil pressure was 27 mm was an ocular hypertensive.

TABLE VII

Ocular Response to a Single Topical Application
of 0.5 Percent (w/v) Timolol Maleate to One Eye
(Treated) of Normal Human Subjects

|  |  | Intraocular Pressure (mm Hg) | |
|---|---|---|---|
| Parameter | Time (hr) | Control Eyes | Treated Eyes |
| Po | 0 | 16.8 ± 0.83 (6) | 16.8 ± 0.83 (6) |
| Po | 5 | 16.8 ± 1.11 (6) | 13.5 ± 1.02 (6) |
| C | 0 | 0.22 ± 0.03 (6) | 0.23 ± 0.04 (6) |
| C | 5 | 0.25 ± 0.04 (6) | 0.24 ± 0.05 (6) |
| F | 0 | 2.8 ± 0.6 (6) | 2.9 ± 0.7 (6) |
| F | 5 | 3.0 ± 0.8 (6) | 2.1 ± 0.8 (6) |

The reported values are the means of the maximal responses based on the time courses of the responses in pairs of eyes of individual subjects. The numbers in parentheses ( ) denote the number of experimental subjects. Po (mm Hg) is the intraocular pressure in seated subjects, C ($\mu$l min$^{-1}$ mm Hg $^{-1}$) is the outflow facility, and F ($\mu$l min$^{-1}$) is the rate of formation of the aqueous humor (subject supine).

The ocular response to α-methyl epinephrine hydrochloride at a concentration of 0.5 percent (w/v) has been studied on two normal subjects and the results are summarized in Table VIII. A significant decrease of intraocular pressure developed in the treated eyes of both subjects within 1 hour and this persisted for more than 5 hours and less than 24 hours. The ocular hypotensive response was not associated with a mydriatic response.

TABLE VIII

The Intraocular Response to a Single Topical Application
of One Drop of 0.5 Percent α-Methyl Epinephrine Hydrochloride
to One Eye (Treated) of Two Human Subjects

|  | 0 Hours | | 1 Hour | | 5 Hours | | 24 Hours | |
|---|---|---|---|---|---|---|---|---|
|  | Control Eye | Treated Eye | Control Eye | Treated Eye | Control Eye | Treated Eye | Control Eye | Treated Eye |
| Intraocular Pressure (mm Hg) | 20 | 20 | 20 | 16 | 20 | 18 | 20 | 20 |
|  | 20 | 20 | 20 | 16 | 19 | 18 | 20 | 20 |
| Pupil Diameter (mm) | 3 | 3 | 3 | 3 | 3 | 3 | 3 | 3 |
|  | 3 | 3 | 3 | 3 | 3 | 3 | 3 | 3 |

The drug was applied unilaterally (treated eye).

The intraocular pressure response to one drop of 0.05 percent (w/v) of dipivaloyl α-methyl epinephrine is illustrated for three normal human subjects in Table IX. It is noted that the intraocular pressure of the treated eye of each subject was decreased at both 1 and 3 hours (T=1 hr., and T=3 hrs., respectively) after treatment (T=0 hr).

TABLE IX

The Effect of a Single Application of One
Drop of 0.05 Percent (w/v) of Dipivaloyl
α-Methyl Epinephrine on the Intraocular
Pressure of Three Human Subjects

| Intraocular Pressure (mm Hg) | | | | | |
|---|---|---|---|---|---|
| 0 Hours | | 1 Hour | | 3 Hours | |
| Control Eye | Treated Eye | Control Eye | Treated Eye | Control Eye | Treated Eye |
| 18 | 18 | 18 | 16 | 18 | 17 |
| 16 | 16 | 15 | 11 | 16 | 11 |
| 16 | 16 | 14 | 11 | 15 | 15 |

The drug was applied unilaterally (treated eye).

The blood pressure and the heart rate of all subjects given the dipivaloyl α-methyl epinephrine were measured prior to and after administration of the drop. No decrease in blood pressure or heart rate was observed.

Dipivaloyl α-methyl epinephrine and its hydrochloride salt are shown to be potent ocular hypotensive drugs. They are significantly more active on a weight or molecular basis than timolol in normal subjects. Each of their durations of response is a function of the dose applied. They act by decreasing the rate of aqueous humor formation and may also increase the outflow facility.

Typical Synthesis of Dipivaloyl

EXAMPLE 1

α-Methyl Norepinephrine Hydrochloride

A typical schematic synthesis of dipivaloyl α-methyl norepinephrine hydrochloride is as follows:

Typical Schematic Synthesis of
Dipivaloyl α-Methyl Norepinephrine Hydrochloride

Step 1

-continued
Typical Schematic Synthesis of
Dipivaloyl α-Methyl Norepinephrine Hydrochloride

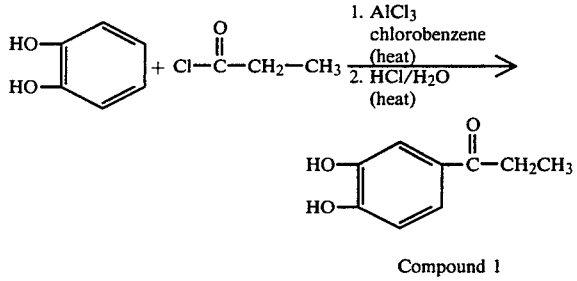

Compound 1

Step 2

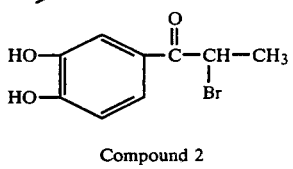

Compound 2

Step 3

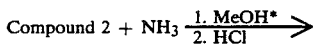

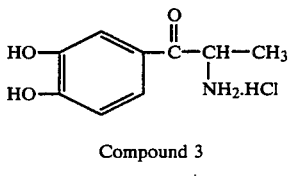

Compound 3

Step 4

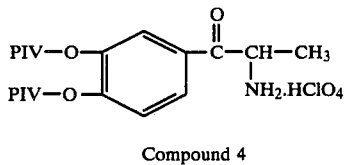

Compound 4

Step 5

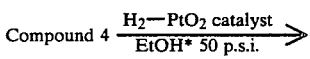

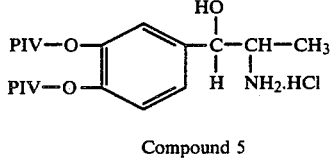

Compound 5

*HOAc = acetic acid;
PIV = pivaloyl, and therefore, PIV—Cl = pivaloyl chloride;
MeOH = methanol; and
EtOH = ethanol.

Step 1, Compound 1

1.5 Moles of commercial catechol in 650 milliliters of dry chlorobenzene is added to 1.9 moles of propionyl chloride and the admixture heated at 50° C. for 30 minutes. The mixture is cooled and 3.2 moles of anhydrous aluminum chloride are added in small portions. The temperature of the resulting admixture is gradually raised to 110° C. and maintained at that temperature for 3 hours. The mixture is hydrolyzed in ice and hydrochloric acid, and the chlorobenzene is thereafter removed by steam distillation. While still warm from the steam distillation, 75 milliliters of concentrated hydrochloric acid and 125 milliliters of toluene are added. After thoroughly cooling, the product (Compound 1) is filtered and washed well with water and toluene.

Compound 1 was reported by Iwao and Samejima, J. Pharm. Soc. Japan, 74, 548–550 (1954) [*Chemical Abstracts*, 49:8174 g (1955)] to have a melting point of 146° C. on recrystallization from water.

Step 2, Compound 2

Following the method of Iwao and Samejina, above, 5 grams of Compound 1 are dissolved in 35 milliliters of glacial ascetic acid and the solution is heated under reflux for 20 minutes in the presence of 4.8 grams of bromine which was previously dissolved in 5 milliliters of acetic acid. The reaction mixture is concentrated under reduced pressure and extracted with diethyl ether. The ether is then removed under reduced pressure and the resulting residue is extracted with benzene to yield Compound 2.

Iwao and Samejima, ibid., report the melting point of Compound 2, after recrystallization from dilute ethanol, to be 151°–152° C.

Step 3, Compound 3

0.3 Moles of Compound 2 are dissolved in 200 milliliters of methanol with warming. The mixture is then agitated at 50°–55° C. for 2 hours in the presence of excess ammonia gas, followed by agitation at room temperature for an additional 24 hour period in the presence of excess gaseous ammonia. The reaction product is converted into the hydrochloride salt by the addition of a minimal amount of concentrated hydrochloric acid to give an acid solution. Refrigeration precipitates the product salt with the addition of 500 milliliters acetone, and Compound 3 is recovered by filtration.

Step 4, Compound 4

0.25 Moles of Compound 3 are dissolved in 500 milliliters ethyl acetate, and 0.50 moles perchloric acid as a 70% aqueous solution are slowly added with continuous stirring. An excess of pivaloyl chloride is added and the resulting admixture is slowly warmed to reflux temperature. The reaction mixture is heated under reflux for about 5 hours and allowed to cool to room temperature with continuous stirring. The product (Compound 4) is precipitated as the perchlorate salt by the addition of 1000 milliliters ether. The precipitated product, Compound 4, is purified and recovered by dissolution in minimal boiling acetone, addition of hexane to the point of incipient turbidity, reprecipitation by refrigeration and filtration.

Step 5, Compound 5

20 Grams of Compound 4 are dissolved in 200 milliliters 95% ethyl alcohol in a Parr reaction vessel with 1.5 gm Adams platinum oxide catalyst, and the mixture is shaken under hydrogen at 50 p.s.i. for 1 hour at room temperature. The mixture is filtered and the ethanol removed on a standard rotary evaporator under reduced pressure. The residue is dissolved in 200 milliliters water; the solution is made basic with ammonium hydroxide and extracted repeatedly with chloroform. The combined chloroform extracts are dried over calcium chloride, filtered, and evaporated. The residue is dissolved in 200 milliliters ether and the product, Compound 5, is precipitated as the hydrochloride salt by passage hydrogen chloride gas into the ether solution. The precipitated product is purified and recovered by dissolution in minimal boiling acetone, addition of hexane to incipient turbidity, refrigeration, and filtration. Compound 5, 3,4-dipivaloyl α-methyl norepinephrine hydrochloride [4-(2-amino-1-hydroxypropyl)-1,2-dipivaloyloxybenzene hydrochloride] is a white crystalline solid freely soluble in water.

Typical Synthesis of Dipivaloyl

EXAMPLE 2

α-Methyl Epinephrine Hydrochloride

A typical schematic synthesis of dipivaloyl α-methyl epinphrine hydrochloride is as follows:

Typical Schematic Synthesis of
Dipivaloyl α-Methyl Epinephrine Hydrochloride

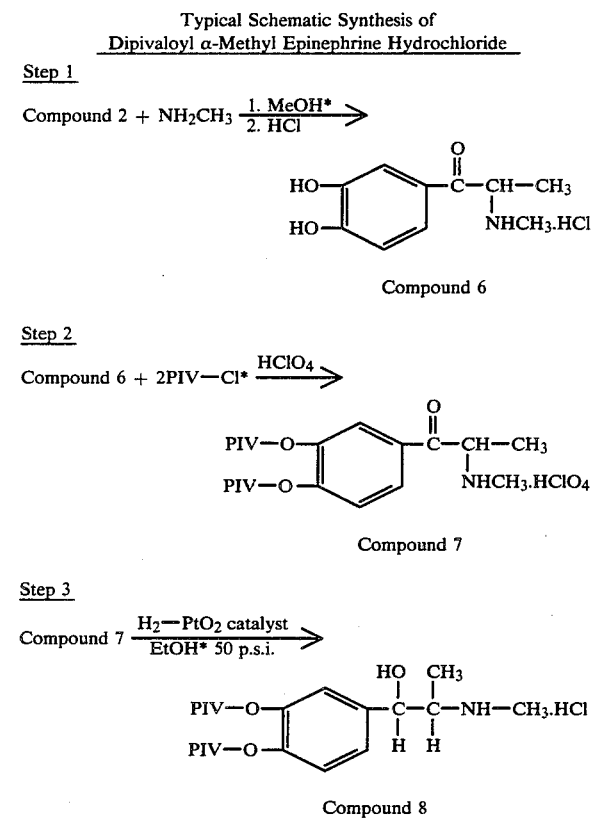

*PIV— = pivaloyl, and therefore, PIV—Cl = pivaloyl chloride; EtOH = ethanol; MeOH = methanol.

Step 1, Compound 6

0.3 Moles of Compound 2 (above) are dissolved in 200 milliliters of methanol with warming. 120 Milliliters of a 40% aqueous solution of methylamine are slowly added thereto, and the mixture stirred at 50°-55° C. for 2 hours. The reaction mixture is then stirred an additional 24 hours at room temperature.

The crude product separates as a solid from the reaction medium and is recovered by filtration. It is then washed well with ether, dissolved in 400 milliliters of 1 normal hydrochloric acid, and approximately 300 milliliters of the aqueous solvent are removed under reduced pressure using a rotary evaporator. The residue is combined with 150 milliliters methanol and filtered through charcoal. The product, Compound 6, is precipitated as the hydrochloride salt by the addition of seven parts of acetone to the methanol solution, is collected by filtration, and dried at 40° C.

Step 2, Compound 7

0.25 Moles of Compound 6 are dissolved in 500 milliliters ethyl acetate and treated as in Step 4 for Compound 4 (above).

Step 3, Compound 8

20 Grams of Compound 7 are treated as in step 5 for Compound 5 (above).

Compound 8, 3,4-dipivaloyl α-methyl epinephrine hydrochloride [4-(2-N-methylamino-1-hydroxypropyl)-1,2-dipivaloyloxybenzene hydrochloride], is one of the novel compounds of this invention.

The present invention has been described generally and with respect to preferred embodiments. It will be clear to those skilled in the art that modifications and/or variations of the disclosed compositions can be made without departing from the scope of the invention set forth herein. The invention is defined by the claims which follow.

I claim:

1. A composition for lowering mammalian intraocular pressure comprising 3,4-dipivaloyl α-methyl epinephrine or the pharmacologically acceptable acid addition salt thereof present in an amount to provide about 0.01 to about 5 milligrams daily when administered about 1 to about 4 times daily, but at less than an amount which would induce substantial mydriasis, together with a ophthalmically acceptable vehicle.

2. The composition of claim 1 wherein the acid of said addition salt is selected from the group consisting of hydrochloride acid, maleic acid and ascorbic acid.

3. A composition for lowering mammalian intraocular pressure comprising 3,4-dipivaloyl α-methyl norepinephrine or the pharmacologically acceptable acid addition salt thereof present in an amount to provide about 0.01 to about 5 milligrams daily when administered about 1 to about 4 times daily, but at less than an amount which would induce substantial mydriasis, together with a ophthalmically acceptable vehicle.

4. The composition of claim 3 wherein the acid of said addition salt is selected from the group consisting of hydrochloride acid, maleic acid and ascorbic acid.

* * * * *